United States Patent
Kamo et al.

(10) Patent No.: US 8,962,695 B2
(45) Date of Patent: Feb. 24, 2015

(54) HYALURONIC ACID PRODUCTION PROMOTER AND MELANIN PRODUCTION INHIBITOR

(75) Inventors: Shuichi Kamo, Tokyo (JP); Shunsuke Suzuki, Tokyo (JP); Toshiro Sato, Tokyo (JP)

(73) Assignee: J-Oil Mills, Inc., Tokyo (JP)

(*) Notice: Subject to any disclaimer, the term of this patent is extended or adjusted under 35 U.S.C. 154(b) by 0 days.

(21) Appl. No.: 13/378,255

(22) PCT Filed: May 25, 2010

(86) PCT No.: PCT/JP2010/058789
§ 371 (c)(1),
(2), (4) Date: Dec. 14, 2011

(87) PCT Pub. No.: WO2010/150612
PCT Pub. Date: Dec. 29, 2010

(65) Prior Publication Data
US 2012/0088939 A1   Apr. 12, 2012

(30) Foreign Application Priority Data

Jun. 22, 2009 (JP) ................................ 2009-147195

(51) Int. Cl.
*A01N 31/00* (2006.01)
*A61K 36/48* (2006.01)
*A61K 8/63* (2006.01)
*A61K 8/97* (2006.01)
*A61K 31/05* (2006.01)
*A61Q 19/02* (2006.01)

(52) U.S. Cl.
CPC . *A61K 36/48* (2013.01); *A61K 8/63* (2013.01); *A61K 8/97* (2013.01); *A61K 31/05* (2013.01); *A61Q 19/02* (2013.01)
USPC .......................................... 514/729; 514/738

(58) Field of Classification Search
None
See application file for complete search history.

(56) References Cited

U.S. PATENT DOCUMENTS

| | | | | |
|---|---|---|---|---|
| 4,371,524 A | * | 2/1983 | Shinohara et al. | 514/33 |
| 6,641,848 B1 | * | 11/2003 | Bonte et al. | 424/757 |
| 6,784,159 B2 | * | 8/2004 | Holub et al. | 514/26 |
| 8,273,906 B2 | * | 9/2012 | Isobe et al. | 549/403 |
| 2002/0193323 A1 | * | 12/2002 | Yegorova | 514/33 |

FOREIGN PATENT DOCUMENTS

| | | | |
|---|---|---|---|
| JP | S533528 | | 1/1978 |
| JP | S6019885 | | 5/1985 |
| JP | H09176036 | | 7/1997 |
| JP | H11302149 | | 11/1999 |
| JP | 2001335454 | | 12/2001 |
| JP | 2005206510 | | 8/2005 |
| JP | 2006028077 | | 2/2006 |
| JP | 2006515303 | | 5/2006 |
| JP | 2007145845 | | 6/2007 |
| JP | 20088222664 | | 9/2008 |
| JP | 2009013084 | | 1/2009 |
| WO | 2007011066 | | 7/2006 |
| WO | 2006106993 | * | 10/2006 |

OTHER PUBLICATIONS

Yoshida, "Functional-Glyco-Materials: Their Development and Application to Foods", CMC Publishing Co., Ltd., Aug. 2008, pp. 323-327.
Russell et al., "Evidence for Structural Changes in Dermatan Sulfate and Hyaluronic Acid with Aging", Carbohydrate Research, 159 (1987), pp. 127-136.
Ghersetich et al., "Hyaluronic Acid in Cutaneous Intrinsic Aging", International Journal of Dermatology, vol. 33, No. 2, Feb. 1994, pp. 119-122.

* cited by examiner

*Primary Examiner* — Karl J Puttlitz
(74) *Attorney, Agent, or Firm* — Edell, Shapiro & Finnan, LLC

(57) ABSTRACT

Provided is a hyaluronic acid production promoter and a melanin synthesis inhibitor. The hyaluronic acid production promoter and the melanin synthesis inhibitor of the present invention each contain soybean saponin as an active ingredient. The soybean saponin is preferably soybean saponin aglycone. The soybean saponin aglycone preferably includes soyasapogenol A and/or soyasapogenol B. The hyaluronic acid production promoter and the melanin synthesis inhibitor of the present invention are each administered transdermally or orally.

4 Claims, No Drawings

HYALURONIC ACID PRODUCTION PROMOTER AND MELANIN PRODUCTION INHIBITOR

TECHNICAL FIELD

The present invention relates to a hyaluronic acid production promoter and a melanin synthesis inhibitor, and more specifically relates to a hyaluronic acid production promoter and a melanin synthesis inhibitor that contain specific soybean-derived components.

BACKGROUND ART

The skin mainly consists of the epidermis, the dermis, and the subcutaneous tissue. The dermis is located beneath the epidermis and is filled with the biological structure called the extracellular matrix constituted of, for example, collagen and hyaluronic acid for supporting the skin structure. The extracellular matrix components are produced by, for example, fibroblasts. In the skin maintaining its youthfulness, production of the extracellular matrix components is accelerated to keep elasticity, moisture, and tension of the skin. It is said that, in contrast, aging of the skin, represented by symptoms such as pigmented spots, wrinkles, sagging skin, and rough skin, progresses with a reduction in extracellular matrix components such as hyaluronic acid.

Hyaluronic acid is one of glycosaminoglycans and is a polymer having a chain structure where glucuronic acid and N-acetyl glucosamine residues are repeatedly linked without having sulfate groups.

Hyaluronic acid is distributed widely throughout the body, for example, in the skin, tendon, muscle, cartilage, brain, and blood vessels. The hyaluronic acid, a main structural component of the extracellular matrix, is known to be present between cells to retain an extracellular fluid and show, for example, a wound healing effect and a joint lubricating effect (Development of functional glyco-material and application to foods, 2005, pp. 324-325). It has been reported that the amount of hyaluronic acid in human skin decreases with aging, and it is supposed that the decrease of hyaluronic acid in the skin is one cause of a reduction in skin elasticity and a decrease in moisture due to aging (Carbohydrate Research, 159(1), 127-136, 1987; International Journal of Dermatology, 33(2), 119-122, 1994).

In order to improve the state due to a decrease in hyaluronic acid, various materials having effects of promoting hyaluronic acid production have been proposed. Examples thereof include retinoic acid, a *Ptychoverpa bohemica* extract (Japanese Patent Laid-Open No. 2008-222664), a saffron extract (Japanese Patent Laid-Open No. 2005-206510), an extract of seaweed belonging to the genus *Durvillea* of the family Durvillea (Japanese Patent Laid-Open No. H9-176036), and a peptide having a specific sequence (Japanese Patent Laid-Open No. 2007-145845).

The retinoic acid is known to be effective, but causes side effects such as dermatitis, and thereby safety issues have been concerned. In plant-derived materials such as the *Ptychoverpa bohemica* extract and the saffron extract or the seaweed extract of the genus *Durvillea* of the family Durvillea, the effects of promoting hyaluronic acid production are not high. With the peptide, it is necessary to intake a large amount of the peptide for obtaining the effect, and thus a satisfactory effect is hardly obtained.

Meanwhile, it is known that soybean isoflavone aglycones promote hyaluronic acid production (Japanese Patent Laid-Open No. 2001-335454). Furthermore, it is known that 20-O-β-D-glucopyranosyl-20(S)-protopanaxadiol (compound K), the main metabolite of ginseng saponin, increases expression of a hyaluronic acid synthase gene to promote hyaluronic acid production (PCT Japanese Translation Patent Publication No. 2006-515303). However, soyasapogenol has not been reported to promote hyaluronic acid production.

There are many unclear points in causes that cause skin pigmentation, such as pigmented spots and freckles, but it is supposed that one cause is enhancement in melanin synthesis function of melanocytes present in the basal epidermal layer, which is triggered by, for example, ultraviolet light or hormone imbalance. When melanocytes are stimulated by stimulus against epidermal cells (keratinocytes), tyrosine in the melanocytes is converted into dopa by action of, for example, tyrosinase, and dopa is further converted into dopaquinone and then into melanin. The synthesized melanin is accumulated in vesicles called melanosome. Melanosomes containing the accumulated melanin are supplied to keratinocytes from melanocytes.

For preventing and improving the above-described skin pigmentation, various materials that inhibit melanin synthesis to achieve whitening effect have been proposed, and examples thereof include ascorbic acid, glutathione, and kojic acid (Japanese Patent Laid-Open No. S53-3538), an *Illicium verum* extract (Japanese Patent Laid-Open No. H11-302149), conagenin (PCT Japanese Translation Patent Republication No. 2007-011066), and acidic oligosaccharide (Japanese Patent Laid-Open No. 2009-13084).

Unfortunately, the ascorbic acid is easily oxidized and therefore has low storability. The glutathione has a drawback of causing a particular off-flavor. The kojic acid has a problem of safety in use at a high concentration. The *Illicium verum* extract, conagenin, and acidic oligosaccharide need high concentrations for showing their effects, and it is not concerned that satisfactory effects are achieved.

Meanwhile, it has been reported that soybean isoflavone inhibits melanin synthesis (Japanese Patent Publication No. S60-19885). It is also known that 2,3-dihydro-3,5-dihydroxy-6-methyl-4H-pyran-4-one and 2,3-dihydro-3,5-dihydroxy-6-methyl-4H-pyran-4-one-binding saponin (DDMP-saponin) inhibits melanin synthesis (Japanese Patent Laid-Open No. 2006-28077). However, the melanin synthesis-inhibiting effects of soybean saponins, other than the DDMP-saponin, and soyasapogenols have not been reported.

SUMMARY OF INVENTION

As described above, among natural products and natural product-derived components, components and products showing hyaluronic acid production-promoting effects and melanin synthesis-inhibiting effects have been searched, but satisfactory results have not been obtained yet. Accordingly, it is an object of the present invention to provide safe and naturally occurring hyaluronic acid production promoter and melanin synthesis inhibitor.

Solution to Problem

The present inventors have diligently studied various natural products to solve the above-mentioned problems and, as a result, have found that soyasapogenol, one of soybean saponins, shows a hyaluronic acid production-promoting effect and a melanin synthesis-inhibiting effect, and have completed the present invention. That is, the present invention provides a hyaluronic acid production promoter including a soybean saponins as active ingredients. Furthermore, the present invention provides a melanin synthesis inhibitor including soybean saponins as active ingredients, other than DDMP-saponin.

The soybean saponin that is used in the hyaluronic acid production promoter or the melanin synthesis inhibitor of the present invention is preferably aglycone.

It is particularly preferred that the aglycone contains soyasapogenol A and/or soyasapogenol B.

The soybean saponins have been already known to exhibit effects of inhibiting fat accumulation (KAWANO-TAKA-HASHI, et al., International Journal of Obesity, 10, 293-302, 1986), inhibiting an increase in blood lipid level (Arichi, et al., Kiso to Rinsho, 16, 135-142, 1982), antioxidant, activating cells, and promoting collagen production (Japanese Patent Laid-Open No. 2006-213649), promoting adiponectin secretion (Japanese Patent Laid-Open No. 2006-143609), inhibiting leptin secretion (Japanese Patent Laid-Open No. 2006-225312), removing abnormal protein (Japanese Patent Laid-Open No. 2002-179592), and inhibiting an increase in blood glucose level (Japanese Patent Laid-Open No. 2005-139114). However, soybean saponins have not been reported to have a hyaluronic acid production-promoting effect or a melanin synthesis-inhibiting effect. Furthermore, there are no reports on hyaluronic acid production-promoting effect and melanin synthesis-inhibiting effect of soyasapogenol A and/ or soyasapogenol B, which are among soyasapogenols in aglycones of soybean saponins.

The hyaluronic acid production promoter and the melanin synthesis inhibitor of the present invention are preferably administered transdermally or orally.

Advantageous Effects of Invention

The hyaluronic acid production promoter and the melanin synthesis inhibitor of the present invention are components derived from soybean, a natural plant, and therefore have high possibility of showing low side effects and can achieve excellent beauty effects by continuous administration for a long time.

DESCRIPTION OF EMBODIMENTS

Preferred embodiments of the hyaluronic acid production promoter and the melanin synthesis inhibitor (hereinafter referred to as hyaluronic acid production promoter or the like) of the present invention will be described in detail. The hyaluronic acid production promoter or the like of the present invention includes soybean saponins as active ingredients.

Soybean saponins can be soybean saponin glycosides or soybean saponin aglycones and are preferably soybean saponin aglycones. Particularly preferred examples of the soybean saponin aglycones include soyasapogenol A and/or soyasapogenol B.

The soybean saponin glycoside can be extracted from cotyledon or germ of soybean or whole soybean by known methods. Specifically, the soybean saponin glycoside is extracted and purified from cotyledon or germ of soybean or whole soybean by methods described in, for example, Japanese Patent Laid-Open No. H03-75939.

Soyasapogenol, the soybean saponin aglycone, can be obtained by removing the carbohydrate chain from the soybean saponin glycoside. Specifically, soyasapogenol is obtained by, for example, acid treatment or enzyme treatment of the soybean saponin glycoside. Soyasapogenol can be chemically synthesized.

The content of the soybean saponins contained in the hyaluronic acid production promoter or the like of the present invention varies according to the form of the composition and the dosage, but is usually in the range of 0.00002 to 100 wt %, preferably 0.0003 to 70 wt %, and most preferably 0.003 to 50 wt %. If the content of the soybean saponin is 0.00002 wt % or less, a sufficient amount for achieving the effect of increasing hyaluronic acid or inhibiting melanin synthesis may not be administered.

The hyaluronic acid production promoter of the present invention may contain, in addition to the soybean saponin as the essential ingredient, a material that is known to increase hyaluronic acid production, for example, one or more of plants such as yacon, crude drugs such as pueraria root, N-acetylglucosamine, peptides, and isoflavone aglycones.

The melanin synthesis inhibitor of the present invention may contain a material that is known to inhibit melanin synthesis, for example, one or more of plants such as *Embelia* of the family Myrsinaceae, crude drugs such as uva-ursi, and L-cysteine.

When the hyaluronic acid production promoter or the like of the present invention is used as a medicine, the medicine may contain auxiliaries that are widely used in medicines, in addition to the soybean saponin as the essential ingredient and the optional hyaluronic acid-producing material and/or the melanin synthesis-inhibiting material. For example, widely used diluent, disintegrant, binder, lubricant, vitamin, xanthine derivative, amino acid, pH adjuster, refreshing agent, suspending agent, thickening agent, solubilizer, antioxidant, coating agent, plasticizer, surfactant, water, alcohol, water-soluble polymer, sweetener, flavoring substance, acidulant, flavor, and colorant can be contained, according to the formulation and the administration route, in the qualitative and quantitative ranges that do not impair the effects of the invention.

The hyaluronic acid production promoter or the like of the present invention is processed into an oral formulation, for example, a solid preparation, such as a powder, granule, capsule, pill, tablet, chewable tablet, or drop pill form, or a liquid preparation, such as a drinkable preparation, solution, suspension, emulsion, syrup, or dry syrup form; or a transdermal formulation, for example, a liquid, solution, emulsion, or cream form, in order for use as a medicine. Soyasapogenol is powder, and, therefore, the desirable form is a solid preparation.

In the case of using hyaluronic acid production promoter or the like of the present invention as a medicine, the administration route is not particularly limited. For example, the administration route is ingestion, dermal uptake, transfusion, or injection (intramuscular, intraperitoneal, subcutaneous, or intravenous). The administration route is preferably ingestion, such as a tablet or a capsule, from the viewpoint of a low burden on patients.

In the case of using the hyaluronic acid production promoter or the like of the present invention as a medicine, the dosage may be appropriately determined depending on the symptoms. In general, in the case of use as a preventive preparation, the dosage of soyasapogenol per day is preferably 0.1 to 100 mg, more preferably 5 to 50 mg. In the case of use as a therapeutic preparation, the dosage per day is preferably 5 to 1200 mg, more preferably 150 to 900 mg.

When the hyaluronic acid production promoter or the like of the present invention is used as cosmetics, the cosmetics may contain auxiliaries that are widely used in cosmetics, in addition to the soybean saponin as the essential ingredient and the optional hyaluronic acid-producing material and/or the melanin synthesis-inhibiting material. Examples of the auxiliary include polyols such as ethylene glycol, polyethylene glycol, propylene glycol, 1,3-butylene glycol, 1,4-butylene glycol, dipropylene glycol, glycerin, diglycerin, polyglycerin, pentylene glycol, isoprene glycol, glucose, maltose, fructose, xylitol, sorbitol, maltotriose, and erythritol; lower alcohols such as methanol, ethanol, propyl alcohol, isopropyl alcohol, butyl alcohol, and isobutyl alcohol; higher fatty acids such as oleic acid, isostearic acid, lauric acid, myristic acid, palmitic acid, stearic acid, behenic acid, and undecylenic acid; fats and oils such as olive oil, corn oil, camellia oil, macadamia nut oil, avocado oil, rapeseed oil, sesame oil, castor oil, safflower oil, cottonseed oil, jojoba oil, coconut oil, and palm oil; waxes such as carnauba wax, candelilla wax, bee wax, and lanoline; saccharides such as sorbitol, mannitol, glucose, sucrose, lactose, and trehalose; thickeners such as carrageenan, xanthan gum, gelatin, pectin, agarose, alginate, dextrin, methyl cellulose, ethyl cellulose, hydroxypropyl cellulose, hydroxyethyl cellulose, carboxymethyl cellulose, carboxyvinyl polymers, polyvinyl alcohols, polyvinylpyrrolidone, gum arabic, karaya gum, tragacanth gum, and tamarind gum; antiseptic agents such as phenoxyethanol, methyl paraben, ethyl paraben, propyl paraben, butyl paraben, paraoxybenzoic acid ester, benzoic acid, salicylic acid and salts thereof, sorbic acid and salts thereof, dehydroacetic acid and salts thereof, chlorocresol, and hexachlorophen; nonionic surfactants such as sodium lauroyl sulfate and polyoxyethylene sorbitan monooleate; anionic surfactants such as alkyl sulfates and sodium n-dodecylbenzenesulfonate; cationic surfactants such as polyoxyethylene dodecylmonomethylammonium chloride; steroid and non-steroid anti-inflammatory agents; vitamins such as vitamin A, vitamin D, vitamin E, vitamin F, and vitamin K; vitamin derivatives such as pyridoxine dicaprylate, pyridoxine dipalmitate, ascorbyl dipalmitate, ascorbyl monopalmitate, and ascorbyl monostearate; antioxidants such as flavonoid and carotenoid; higher aliphatic hydrocarbons such as squalane, squalene, and liquid paraffin; sphingolipids such as ceramide, cerebroside, and sphingomyelin; sterols such as cholesterol and phytosterol; silicones such as methylpolysiloxane, methylphenylpolysiloxane, methylcyclopolysiloxane, octamethylcyclotetrasiloxane, octamethylcyclopentasiloxane, decamethylcyclopentasiloxane, and methylhydrogenpolysiloxane; ultraviolet absorbers such as paraaminobenzoic acid, monoglycerin paraaminobenzoate, methyl anthranilate, homomenthyl-N-acetylanthranilate, octyl paramethoxycinnamate, ethyl-4-isopropyl cinnamate; minerals such as bentonite, smectite, beidellite, nontronite, saponite, hectorite, sauconite, and stevensite; inorganic pigments such as red iron oxide, yellow iron oxide, black iron oxide, cobalt oxide, ultramarine pigments, iron blue pigments, titanium oxide, and zinc oxide; colorants such as Red No. 202, Yellow No. 4, and Blue No. 404; flavors; balms, etc.

The hyaluronic acid production promoter or the like of the present invention is processed into a transdermal formulation, for example, a liquid, solution, emulsion, milky liquid, cream, or powder form; or an oral formulation, for example, a solid preparation, such as a powder, granule, capsule, pill, tablet, chewable tablet, or drop pill form, or a liquid preparation, such as a drinkable preparation, solution, suspension, emulsion, syrup, or dry syrup form, in order for use as cosmetics.

In using the hyaluronic acid production promoter or the like of the present invention is used as cosmetics, the administration route is ingestion or dermal uptake. From the viewpoint of fast-acting cosmetics, dermal uptake in the form of solution, emulsion, milky liquid, or cream is preferable.

In the case of using the hyaluronic acid production promoter or the like of the present invention as cosmetics, the dosage of soyasapogenol per day is preferably 0.001 to 100 mg, more preferably 0.05 to 50 mg.

When the hyaluronic acid production promoter or the like of the present invention is used as a functional food, the functional food may contain additives that are widely used in functional foods, in addition to the soybean saponin as the essential ingredient and the optional hyaluronic acid-producing material and/or the melanin synthesis-inhibiting material. For example, widely used diluent, disintegrant, binder, lubricant, vitamin, xanthine derivative, amino acid, pH adjuster, refreshing agent, suspending agent, thickening agent, solubilizer, antioxidant, coating agent, plasticizer, surfactant, water, alcohol, water-soluble polymer, sweetener, flavoring substance, acidulant, flavor, and colorant can be contained, according to the form of the oral formulation, in the qualitative and quantitative ranges that do not impair the effects of the invention.

The hyaluronic acid production promoter or the like of the present invention is processed into an oral formulation, for example, a solid preparation, such as a powder, granule, capsule, pill, tablet, chewable tablet, or drop pill form, or a liquid preparation, such as a drinkable preparation, solution, suspension, emulsion, syrup, or dry syrup form, in order for use as a supplement and functional food. Soyasapogenol is powder, and, therefore, the desirable form is a tablet.

The hyaluronic acid production promoter or the like of the present invention may be directly mixed with ingredients during processing of general processed foods such as bread, cooked rice, soup, prepared food, confectionery, or candy.

In the case of adding the hyaluronic acid production promoter or the like of the present invention to a supplement, functional food, health food, or common food, the dosage of soyasapogenol per day is preferably 0.1 to 100 mg, more preferably 5 to 50 mg, in view of safety.

Composition examples of the hyaluronic acid production promoter or the like of the present invention are shown below, but the present invention is not limited thereto.

Composition Example 1

Tablet

TABLE 1

| Composition | Dosage (parts by weight) |
| --- | --- |
| Corn starch | 40 |
| Crystalline cellulose | 20 |
| Carboxymethyl cellulose | 10 |
| Soyasapogenol | 0.1 |
| Lactose | balance |
| Total | 100 |

Composition Example 2

Capsule

TABLE 2

| Composition | Dosage (parts by weight) |
| --- | --- |
| Olive oil | 90 |
| Bee wax | 2 |
| Glycerin | 2 |
| Soyasapogenol | 0.1 |
| Lactose | balance |
| Total | 100 |

Composition Example 3

Skin Lotion

TABLE 3

| Composition | Dosage (parts by weight) |
| --- | --- |
| Ethanol | 10 |
| Glycerin | 3 |
| Propylene glycol | 3 |
| Soyasapogenol | 0.01 |
| Flavor/antiseptic agent | proper quantity |
| Purified water | balance |
| Total | 100 |

Composition Example 4

Cream

TABLE 4

| Composition | Dosage (parts by weight) |
| --- | --- |
| Squalane | 10 |
| Glycerin | 10 |
| Liquid paraffin | 5 |
| Cetanol | 3 |
| Stearic acid | 2 |
| Lanolin | 2 |
| Soyasapogenol | 0.01 |
| Flavor/antiseptic agent | proper quantity |
| Purified water | balance |
| Total | 100 |

EXAMPLES

The present invention will be described in more detail with reference to examples below, but is not limited thereto.

Preparation Example 1

Production of soyasapogenol 1600 mL of methanol containing 3% hydrochloric acid was added to 50 g of a commercially available soybean saponin preparation (saponin AZ-B: 31.9% of group A saponin and 52.9% of group B saponin, manufactured by J-Oil Mills, Inc.), and the resulting mixture was retained at 70° C. for 3 hours. After that, 4000 mL of water was added to the reaction mixture, followed by filtration. To the residue on the filter paper, 500 mL of water was added, and the mixture was neutralized with 4 N and 0.1 N sodium hydroxide solutions. Filtration was performed again, and water was further added to the residue on the filtration paper. The resulting mixture was dried to obtain 15.3 g of soyasapogenol powder.

The concentration of soyasapogenol in the powder was measured according to the method of Rupashinghe, et al. (J. Agric. Food Chem., 51, 5888-5894, 2003) to confirm that the concentration of soyasapogenol A was 27.3% and that the concentration of soyasapogenol B was 49.8%.

Example 1

Hyaluronic Acid Production Promoter

The hyaluronic acid production-promoting effect of soyasapogenol was tested by using normal human fibroblasts by the following procedure.

1. Testing Method

Normal human fibroblasts (manufactured by Kurabo Industries, Ltd.) were inoculated to a 96-well plate at a cell density of $2.0 \times 10^4$ cells per well. The medium was exchanged 24 hours after the inoculation with Dulbecco's Modified Eagle's medium (DMEM) containing 0.5 wt % of fetal bovine serum (FBS) containing the soyasapogenol powder at concentrations shown in Table 5. The validity of the testing method was confirmed by using 5% FBS-containing DMEM as a positive control. After culturing in the medium containing the sample for 48 hours, the medium supernatant was collected and was subjected to ELISA for measuring the amount of hyaluronic acid. The cells were dissolved by a solution of 0.5% Triton X-100, and then the amount of protein was quantitatively measured.

2. Measurement of Hyaluronic Acid Amount

The amount of hyaluronic acid in medium supernatant was measured by the following method. A hyaluronic acid solution was put to an ELISA plate, and coating was performed at 37° C. for 1 hour. Then, blocking with a 1% bovine serum albumin (BSA) solution was performed at 4° C. overnight. A primary antibody reaction by a 1% BSA solution containing a biotin-labeled hyaluronic acid-binding protein (manufactured by Seikagaku Corp.) and the medium supernatant diluted with a phosphate buffer saline (PBS) or hyaluronic acid for a standard curve was performed at 37° C. for 1 hour. After washing, horseradish peroxidase-labeled streptavidin (R&D System, Inc.) diluted with a 1% BSA solution was reacted at 37° C. for 1 hour. Then, 0.3 mg/mL of 2,2'-azinobis (3-ethylbenzothiazoline-6-sulfonic acid) diammounium salt (ABTS) and phosphate-citrate buffer solution (0.1 M, pH 4.0) containing 0.03% of hydrogen peroxide solution were added thereto, followed by reaction for 20 minutes. The absorbance at 405 nm was measured with a microplate reader.

The amount of hyaluronic acid in the medium was determined from a standard curve obtained by using the same ELISA plate, and the amount of produced hyaluronic acid per unit protein amount was calculated by dividing the hyaluronic acid amount in the medium by the total protein content of the cells to evaluate the hyaluronic acid production-promoting effect.

Table 5 shows the results of evaluation of the hyaluronic acid production-promoting effect of the soyasapogenol powder on human fibroblasts as relative values compared with the amount assumed to be 100 of produced hyaluronic acid per unit protein amount in sample-free control. The sample groups were each tested at n=6, the mean values thereof are shown as the results. As statistical processing, Student's t-test compared to the sample-free control group was performed, and a significance level less than 5% was indicated by *, and a significance level less than 1% was indicated by **.

TABLE 5

| Soyasapogenol powder concentration (μg/mL) | Amount of produced hyaluronic acid (relative value) | t-Test |
| --- | --- | --- |
| 0 | 100.0 | |
| 3.13 | 128.1 | ** |

TABLE 5-continued

| Soyasapogenol powder concentration (µg/mL) | Amount of produced hyaluronic acid (relative value) | t-Test |
|---|---|---|
| 6.25 | 129.4 | ** |
| 12.50 | 137.7 | ** |
| 25.00 | 147.4 | ** |
| 50.00 | 167.4 | ** |
| 100.00 | 180.9 | ** |
| 200.00 | 183.3 | ** |

As shown in Table 5, the hyaluronic acid production-promoting effect was increased with an increase in concentration of the soyasapogenol powder. Even at a low soyasapogenol powder concentration of 3.13 µg/mL, a significant hyaluronic acid production-promoting effect at a significance level less than 1% compared to negative control was confirmed. This revealed that soyasapogenol shows a hyaluronic acid production-promoting effect in human fibroblasts.

Example 2

Melanin Synthesis Inhibitor

The melanin synthesis-inhibiting effect of soyasapogenol was tested using B16 mouse melanoma cells by the following procedure.

1. Testing Method

A B16 mouse melanoma F0 cell line (B16F0) was inoculated to a 6-well plate at a cell density of $2.0 \times 10^3$ cells per well using a Dulbecco's Modified Eagle's medium (DMEM/5) containing 5% of fetal bovine serum (FBS). After culturing for 24 hours, the medium was exchanged with DMEM/5 containing the soyasapogenol powder used in Example 1 at concentrations shown in Table 6. The validity of the testing method was confirmed by culturing DMEM/5 containing 50 mM of sodium lactose as a positive control. After culturing for 6 days, the cells were exfoliated with trypsin to prepare a cell pellet.

2. Visual Judgment

The color tone of each cell pellet was visually evaluated and scored into five grades. One of which color tone is white was score as 1, and the score was increased with the color tone getting black so that the most black one was scored as 5.

3. Measurement of Melanin Amount

The cell pellet was washed with a PBS (−) solution containing 5% trichloroacetic acid, an ethanol/diethyl ether solution (3/1, v/v), and diethyl ether in this order, and was then dissolved in 1 N sodium hydroxide at 100° C. for 5 minutes. The absorbance at 430 nm was measured with a microplate reader. The amount of melanin was calculated using a standard curve prepared using synthetic melanin (manufactured by Sigma-Aldrich Japan K.K.) as a standard material. The amount of protein was measured, and the amount of melanin per unit protein amount was calculated by dividing the amount of melanin by the total protein content of the cells.

Table 6 shows the results of evaluation of the melanin synthesis-inhibiting effect of the soyasapogenol powder on mouse B16 melanoma cells as relative values compared with the amount assumed to be 100 of synthesized melanin per unit protein amount in control. The sample groups were each tested at n=3, the mean values thereof are shown as the results. As statistical processing, Student's t-test compared to the sample-free control group was performed, and a significance level less than 5% was indicated by *, and a significance level less than 1% was indicated by **.

| Soyasapogenol powder concentration (µg/mL) | Whiteness score | Synthesized melanin amount (relative value) | t-Test |
|---|---|---|---|
| 0 | 4 | 100.0 | |
| 0.04 | 4 | 89.0 | |
| 0.20 | 3 | 73.0 | ** |
| 1.00 | 3 | 70.9 | ** |
| 5.00 | 3 | 57.3 | ** |

As shown in Table 6, the melanin synthesis-inhibiting effect was increased with an increase in sample concentration. Even at a low soyasapogenol powder concentration of 0.20 µg/mL, a significant melanin synthesis-inhibiting effect at a significance level less than 1% compared to negative control was confirmed. In addition, whiteness score was improved even at a low soyasapogenol powder concentration of 0.20 µg/mL. Thus, the melanin synthesis-inhibiting effect of soyasapogenol in melanoma cells was revealed.

The invention claimed is:

1. A method of inhibiting the synthesis of melanin, comprising the step of administrating a formulation comprising an effective amount of soybean saponin aglycone as an active ingredient to a person to inhibit the synthesis of melanin, wherein the person suffers from skin pigmentation and is in need of inhibiting the synthesis of melanin and the soybean saponin aglycone comprises soyasapogenal A, and the formulation is an oral formulation.

2. The method according to claim 1, wherein the soybean saponin aglycone further comprises soyasapogenol B.

3. The method according to claim 1, wherein the formulation further comprises at least one of yacon, pueraria root, N-acetylglucosamine, peptides, and isoflavone aglycones.

4. The method according to claim 1, wherein the formulation further comprises at least one of Embelia of the family Myrsinaceae, uva-ursi, and L-cysteine.

* * * * *